United States Patent [19]

Jackson

[11] Patent Number: 4,850,969
[45] Date of Patent: Jul. 25, 1989

[54] RETROPERFUSION CATHETER AND TIP CONSTRUCTION FOR USE THEREWITH

[75] Inventor: Jerome Jackson, Los Angeles, Calif.

[73] Assignee: Retroperfusion Systems, Inc., Costa Mesa, Calif.

[21] Appl. No.: 154,921

[22] Filed: Feb. 11, 1988

Related U.S. Application Data

[63] Continuation-in-part of Ser. No. 103,495, Oct. 1, 1987, abandoned.

[51] Int. Cl.⁴ ............................................. A61M 29/00
[52] U.S. Cl. ....................................... 604/96; 604/102
[58] Field of Search ................. 604/96, 102, 100, 101, 604/247, 264; 128/344

[56] References Cited

U.S. PATENT DOCUMENTS

| | | | |
|---|---|---|---|
| 2,531,730 | 11/1950 | Henderson | 604/264 |
| 3,674,014 | 7/1972 | Tillander | 604/264 |
| 3,963,028 | 6/1976 | Cooley et al. | 604/264 |
| 4,029,104 | 6/1977 | Kerber | 604/96 |
| 4,204,328 | 5/1980 | Kutner | 604/256 |
| 4,405,313 | 9/1983 | Sisley et al. | 604/264 |
| 4,496,345 | 1/1985 | Hasson | 604/102 |
| 4,601,706 | 7/1986 | Aillon | 604/102 |
| 4,689,041 | 8/1987 | Corday et al. | 604/99 |
| 4,712,551 | 12/1987 | Rayhanabad | 604/101 |
| 4,725,264 | 2/1988 | Glassman | 604/102 |
| 4,737,152 | 4/1988 | Alchas | 604/9 |

FOREIGN PATENT DOCUMENTS

| | | | |
|---|---|---|---|
| 2737855 | 3/1979 | Fed. Rep. of Germany | 604/102 |
| 2069339 | 8/1981 | United Kingdom | 604/9 |

*Primary Examiner*—John D. Yasko
*Attorney, Agent, or Firm*—Flehr, Hohbach, Test, Albritton & Herbert

[57] ABSTRACT

Retroperfusion catheter comprising a flexible elongate element having proximal and distal extremities and having at least first and second lumens extending therethrough. A flexible tip is secured to the distal extremity of the flexible elongate element. A balloon having proximal and distal portions is secured to the distal extremity of the flexible elongate element. The distal extremity of the balloon overlies a portion of the flexible tip and secures the flexible tip to the distal extremity of the flexible elongate member to ensure that the flexible tip will not become separated from the distal extremity of the flexible elongate element.

12 Claims, 3 Drawing Sheets

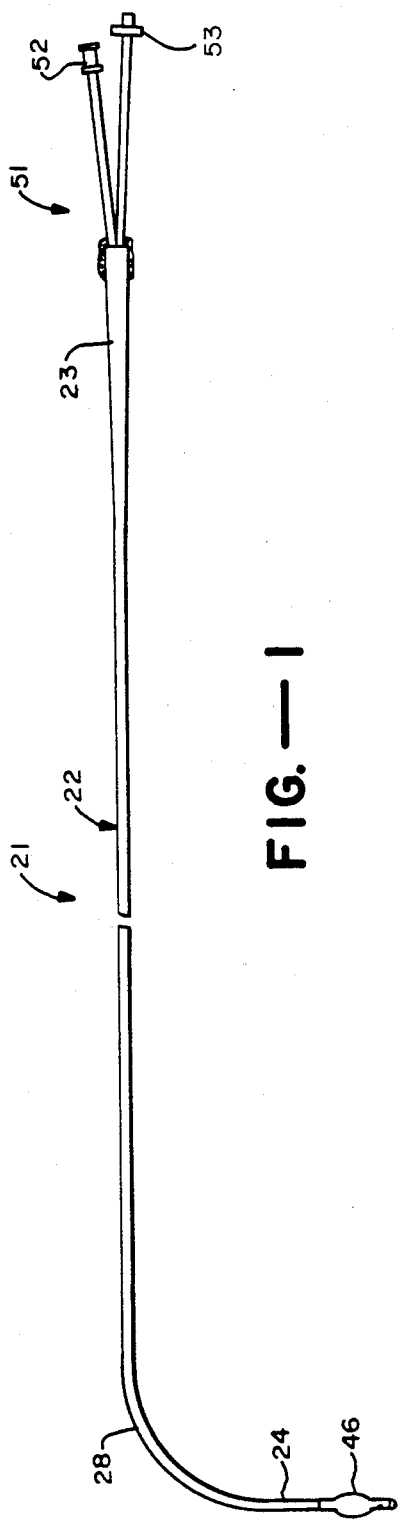
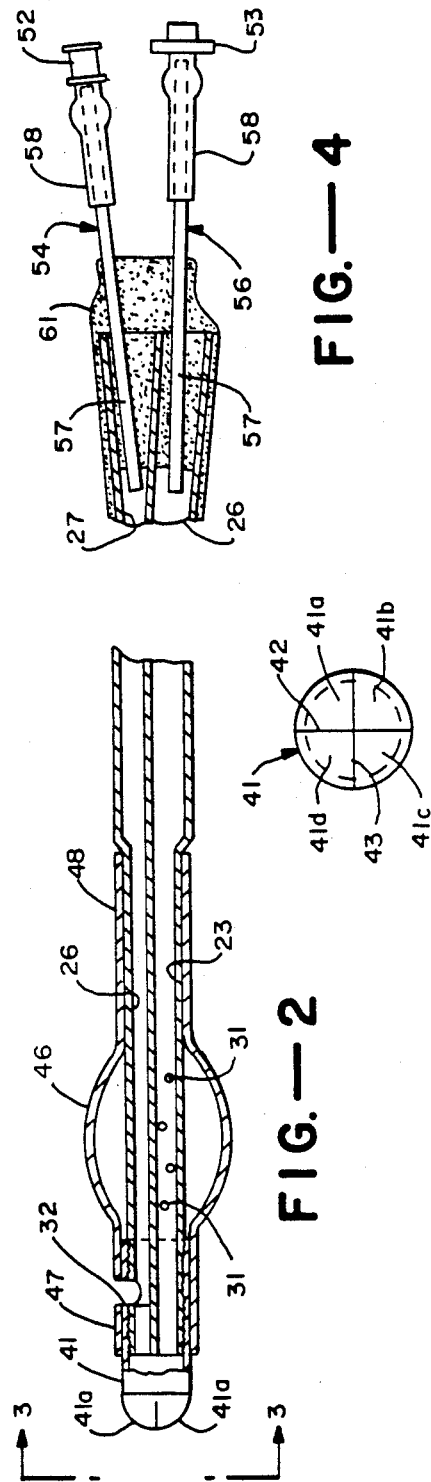

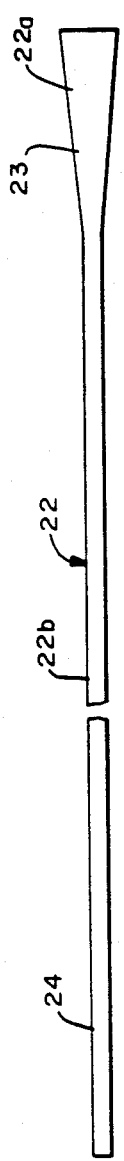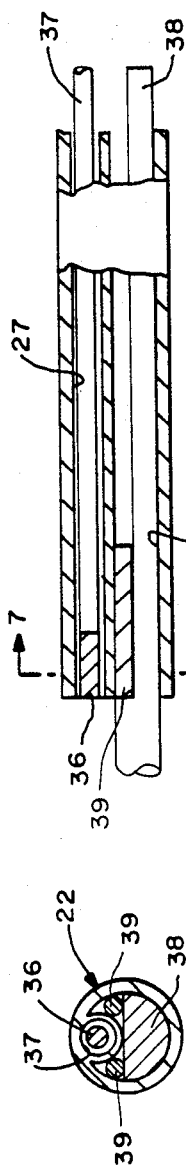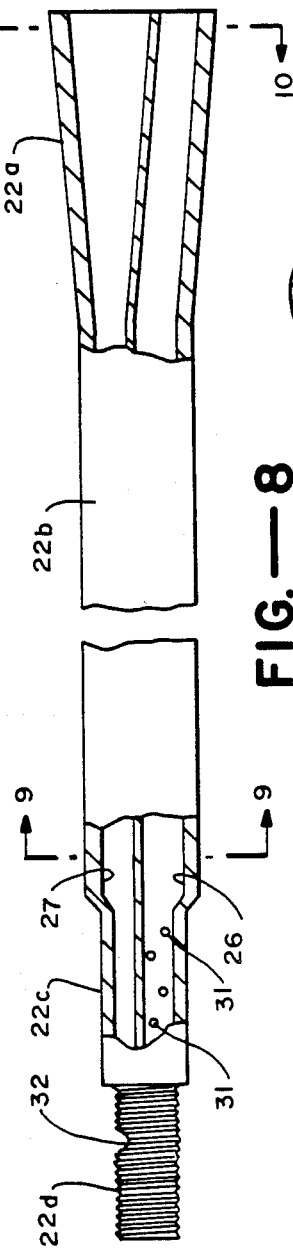

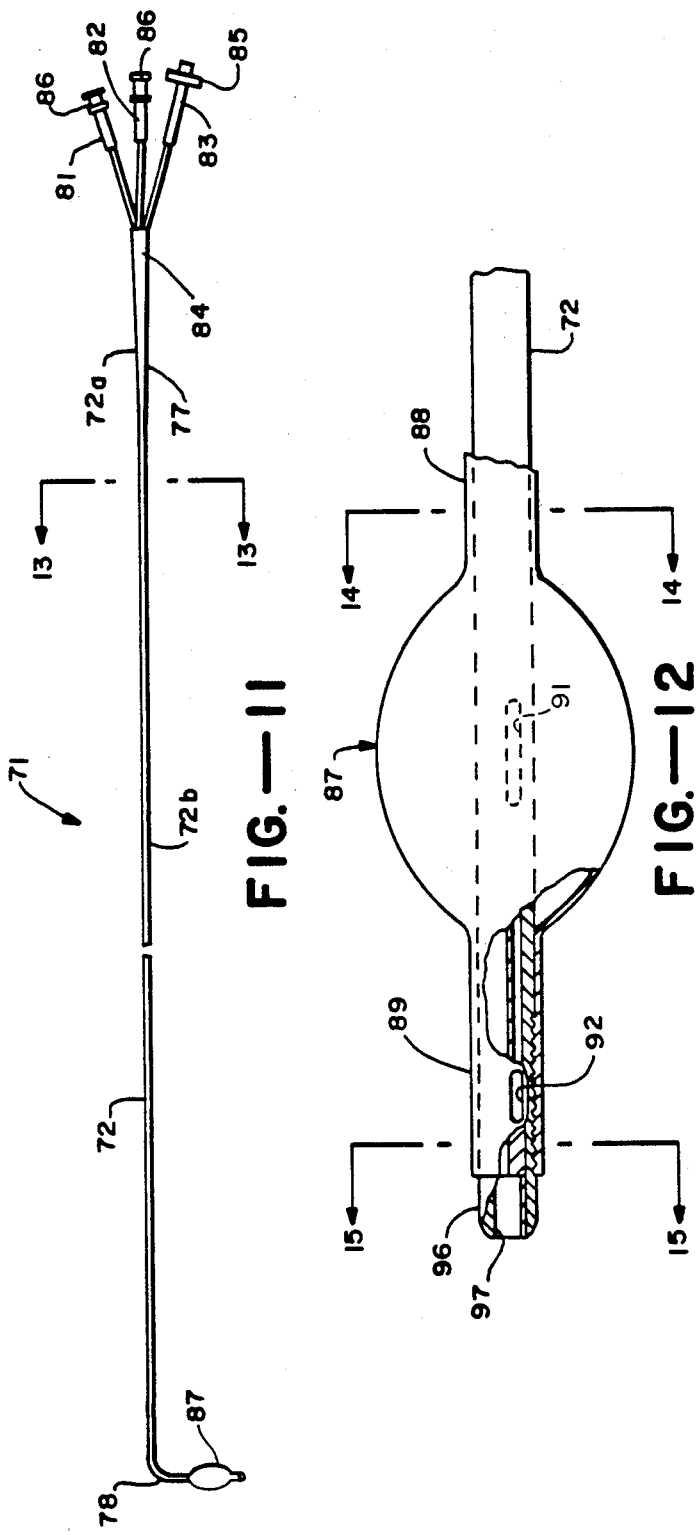
FIG.—11  FIG.—12  FIG.—13  FIG.—14  FIG.—15

RETROPERFUSION CATHETER AND TIP CONSTRUCTION FOR USE THEREWITH

This application is a continuation-in-part application of Ser. No. 103,495 filed on Oct. 1, 1987, now abandoned.

This invention relates to retroperfusion catheters and more particularly, to a tip construction for retroperfusion catheters. Retroperfusion catheters have heretofore been provided which have utilized auto-inflatable balloons and alternatively, non-auto-inflatable balloons. Such catheters have generally had open ends which permitted bidirectional flow permitting undesirable mixing of venous blood with arterial blood. Such a construction also hindered rapid and complete deflation of the balloon. There is therefore a need for a new and improved retroperfusion catheter and a tip construction for use therewith.

In general, it is an object of the present invention to provide a retroperfusion balloon catheter having a tip construction which is relatively soft and flexible.

Another object of the invention is to provide a catheter of the above character having a tip construction which includes a tip valve movable between open and closed positions.

Another object of the invention is to provide a catheter of the above character that is of the autoinflatable type which minimizes reverse flow.

Another object of the invention is to provide a catheter of the above character which facilitates rapid and complete balloon deflation.

Another object of the invention is to provide a catheter of the above character which inhibits mixing of venous blood with arterial blood.

Another object of the invention is to provide a catheter of the above character which minimizes abrasion of the venous vessel and the possibility of puncturing a venous vessel during insertion of the catheter into the vessel.

Another object of the invention is to provide a catheter of the above character having a tip construction with a plurality of redundant features to prevent the tip from becoming separated from the distal extremity of the catheter.

Another object of the invention is to provide a catheter of the above character in which the tip construction provides a minimum resistance to forward flow of retroperfusion blood.

Another object of the invention is to provide a catheter having tip construction of the above character which is lightly biased into a closed position so as to provide a minimum of resistance to forward flow of retroperfusion blood.

Another object of the invention is to provide a catheter of the above character in which the tip construction is of such a character that a guidewire can be introduced and retracted through the tip construction without difficulty.

Another object of the invention is to provide a catheter of the above character which can be utilized with an auto-inflatable balloon or alternatively, a non-auto-inflatable balloon.

Another object of the invention is to provide a catheter of the above character in which pressure measurements can be accurately made without substantial interference from the retroperfusion blood flow.

Additional objects and features of the invention will appear from the following description in which the preferred embodiments are set forth in detail in conjunction with the accompanying drawings.

FIG. 1 is a plan view of a retroperfusion catheter incorporating the present invention.

FIG. 2 is a greatly enlarged cross-sectional view of the distal extremity of the catheter shown in FIG. 1.

FIG. 3 is a view looking along the line 3—3 of FIG. 2.

FIG. 4 is a greatly enlarged cross-sectional view of the proximal extremity of the catheter shown in FIG. 1.

FIG. 5 is a side elevational view of the flexible elongate double lumen member utilized in the construction of the catheter shown in FIG. 1.

FIG. 6 is an enlarged view partly in cross-section of the member shown in FIG. 5 before the forming operation.

FIG. 7 is a cross-sectional view taken along the line 7—7 of FIG. 6.

FIG. 8 is an enlarged detail view partially in cross section showing the flexible elongate member after forming.

FIG. 9 is a cross-sectional view taken along the line 9—9 of FIG. 8.

FIG. 10 is a cross-sectional view taken along the line 10—10 of FIG. 8.

FIG. 11 is a plan view of a three lumen retroperfusion catheter incorporating another embodiment of the present invention.

FIG. 12 is an enlarged detail view partially in cross section of the distal extremity of the catheter shown in FIG. 11.

FIG. 13 is a cross-sectional view taken along the line 13—13 of FIG. 11.

FIG. 14 is a cross-sectional view taken along the line 14—14 of FIG. 12.

FIG. 15 is a cross-sectional view taken along the line 15—15 of FIG. 12.

In general, the retroperfusion catheter of the present invention is comprised of a flexible elongate element having proximal and distal extremities with first and second lumens extending therethrough. A flexible tip is secured to the distal extremity of the flexible elongate element. A balloon is secured to the distal extremity of the flexible elongate element and has a distal extremity overlying a portion of the flexible tip and serving to secure the flexible tip to the distal extremity of the flexible elongate element to ensure that the flexible tip will not become separated from the distal extremity of the flexible elongate element. Additional or redundant attaching means is provided for securing the flexible tip to the flexible elongate element and includes an adhesive between the portion of the flexible tip and the distal extremity of the balloon and screw-like means plus additional adhesive disposed between the portion of the flexible tip valve and the flexible elongate element. For an auto-inflatable balloon, the flexible tip includes a valve movable between open and closed positions. A flow passage is provided in the flexible elongate element and is in communication with the balloon and is in communication with the first lumen. The flow passage extends to the valve in the tip. A side port is provided proximal of the flexible tip and distal of the balloon and in communication with the second lumen to make possible pressure monitoring.

More specifically, the retroperfusion catheter of the present invention as shown in FIGS. 1–10 consists of a double lumen retroperfusion catheter 21. The double lumen retroperfusion catheter 21 consists of a flexible elongate tubular member 22 formed of a suitable plastic material, as for example, a material known as PeBax which is basically a modified combination of polyethylene and nylon. The member 22 has an enlarged conically-shaped portion 22a and an intermediate cylindrical portion 22b. It is provided with proximal and distal extremities 23 and 24. The tubular member 22 is formed in a suitable manner such as by extruding to provide at least two lumens 26 and 27 therein as shown in FIG. 9. The lumen 26 is a large lumen crescent-shaped in cross-section, whereas the lumen 27 is a small lumen circular in cross-section. As can be seen, the lumen 27 extends in from one side wall of the flexible elongate member 22 in towards the central axis lumen so as to provide the crescent-shaped lumen 26.

The flexible elongate tubular member 22 can be of a suitable size, as for example, 8 French and having an outside diameter of approximately 105 inches and an inside cross-sectional area corresponding diameter in a tube of approximately 0.090 inches. The distal extremity of the catheter 24 is provided with a bend 28 to facilitate positioning of the catheter.

The flexible elongate tubular member 22 has a suitable length, as for example, 24 inches. The proximal extremity 23 has an outside diameter of approximately 0.200 inches. The tubular member 22 has a wall thickness at the upper extremity of the same where the lumen 27 passes as shown in FIG. 10 of approximately 0.023 inches and a wall thickness on the lower side of approximately 0.010 inches. The inner lumen 27 also shown in FIG. 10 is formed by a wall thickness of approximately 0.010 inches with an inside diameter of 0.097 inches and an outside diameter of 0.130 inches. From the distal extremity of the flexible elongate tubular member 22, it can be seen that a taper is provided to form the tapered portion 22a which can have a length ranging from 3 to 5 inches. The cylindrical portion 22b has a suitable length as, for example, 20–48 inches to provide a total length of approximately 23 to 53 inches. The tubular portion 22b has a suitable outside diameter of approximately 0.105 inches. The necked-down portion 22c is of a smaller diameter, as shown in FIG. 8, as for example, 0.091 inches. The upper portion of the flexible tubular member adjacent the lumen 27 as shown in FIG. 8 is provided with a wall thickness of approximately 0.010 inches at the upper extremity and a wall thickness of approximately 0.008 inches at the lower extremity. The lumen 27 is formed by a wall thickness of approximately 0.006 inches. It has an outside diameter of 0.040 inches and an inside diameter of 0.027 inches. The flexible tubular member 22 is also provided with a threaded portion 22d on its distal extremity having a length of approximately 0.250 inches.

A plurality of spaced apart holes 31 are provided in the portion 22c of the elongate tubular member 22 are provided for inflation purposes as hereinafter described. The holes 31 are spaced apart by a suitable distance, as for example, 0.100 inches on centers. A suitable number of holes can be provided, as for example, four holes as shown in FIG. 7 and can have a suitable diameter as, for example, 0.039 inches. The holes can be arranged in a suitable manner in the portion 22c. For example, they can be spaced apart longitudinally of the portion 22c and also can be spaced circumferentially of the portion 22c. All of the holes 31 open into the main blood flow lumen 26. It should be appreciated that if desired a slot (not shown) can be provided in the portion 22c instead of the holes 31.

An additional hole or port 32 is formed in the threaded portion 22b and opens into the lumen 27. The lumen 27 is plugged at the distal extremity by a plug 36 having a suitable length, as for example, 0.100 inches, as shown, particularly in FIGS. 6 and 7.

Preparatory to the forming operation to provide the catheter construction which is shown in FIG. 7, a mandrel 37 of a suitable diameter such as 0.025 inches is placed in the small lumen 27 and a larger D-shaped mandrel 38 formed from a rod having a suitable diameter such as 0.074 inches which is ground down on one side to provide a depth of 0.038 inches. The mandrel 38 is placed in the lumen 26 as shown in FIGS. 6 and 7. The mandrel 37 is advanced in the lumen 27 until it is in engagement with the plug 36. The mandrel 38 is positioned so it extends through the portion 22c of the tubular member 22 where the mandrel meets the crescent-shaped portion of lumen 26 as shown in FIG. 9. A pair of additional plugs 39 of a suitable length, as for example, 0.300 inches are placed in the lumen 26 on opposite sides of the mandrel 38 as shown in FIGS. 6 and 7 to occupy additional portions of the space in the lumen 26.

The flexible elongate tubular member 22 is formed of a plastic as hereinbefore described which can be shaped upon the application of heat. The distal extremity of the tubular member 24 is placed in a mold with heat and drawn to form the threaded portion 22d and portion 22c with the mandrels 37 and 38 therein and with the plugs 36 and 39 therein. After the forming operation has been completed, the mandrels 37 and 38 can be removed. The plugs 39 are formed of plastic and melt with the application of heat and form a part of the member 22. The plug 36 can also be fastened in place by a suitable means such as by an adhesive.

A tip valve 41 is secured to the distal extremity of the flexible elongate member 22. The tip valve 41 is formed of a suitable material such as a silicone elastomer. It is generally cylindrical with a hemispherical distal extremity in which there are provided four leaflet portions 41c, 41b, 41c and 41d, each of which subtend approximately 90°. The leaflet portions are formed by two slits 42 and 43 provided in the hemispherical portion of the tip valve extending at right angles to each other. During the molding of the tip valve, the tip valve is also provided with molded threads at its proximal extremity which are adapted to mate with the threaded portion 22d of the flexible elongate member 22. The threaded portions of the tip valve 41 and the threaded portion 22d of the flexible elongate member interlock to form a mechanical bond between the tip valve and the flexible elongate member 22. The threaded tip valve 41 can have a suitable length as, for example, 0.375 inches and an outside diameter of 0.094 inches and an inside diameter of 0.078 inches. The slits 42 and 43 can have a depth of approximately 0.040 inches plus or minus 0.015 inches. The threaded interior of the tip valve 41 and the threaded portion 22d of the flexible elongate member 22 are preprimed with a suitable primer and then a silicone rubber adhesive is applied over the threaded portion 22d. The tip valve 41 is then mounted thereon to extend over the threaded portion 22d as shown in FIG. 2. In this manner it can be seen that the tip valve is permanently secured to the distal extremity of the flexible elongate member 22. Thus two means of attachment are provided. One is the use of the threads on the threaded portion 22d and on the tip valve 41 and the other is the silicone adhesive which is utilized. In other words two levels of redundancy are provided for securing the tip valve 41 to the distal extremity of the flexible elongate member 22 to ensure that the tip valve cannot accidentally become dislodged from the flexible elongate member 22.

A flexible balloon or bladder 46 is provided which is formed of a suitable material such as a heat shrinkable polyethylene. The outside diameter of the balloon can range from approximately 3 millimeters to 20 millimeters depending upon the use for the same. The length of the balloon can range from ½ inch to approximately one inch. The distal extremity 47 of the balloon 46 is secured to the distal extremity of the flexible elongate member 22 over the threaded portion of the tip valve 41 and is secured thereto. This is accomplished by applying a suitable adhesive such as a cyanoacrylate adhesive over the exterior of the threaded tip valve 41. The distal extremity 47 of the balloon 46 is then positioned over the threaded portion of the tip valve 41 and is shrunk onto the threaded portion of the tip valve 41 by the application of heat. This results in a further mechanical attachment for the tip valve because of the compression forces applied by the shrink tubing utilized for the balloon 46 as well as the adhesive which is applied between the distal extremity 47 of the balloon 46 and the threaded portion of the tip valve 41. Thus there are provided at least three independent means for redundantly attaching the tip valve 41 to the distal extremity of the flexible elongate member 22. The proximal extremity 48 of the balloon 46 is secured to the portion 22b of the flexible elongate member so that the openings 31 in the flexible elongate element 22 open into the balloon 46 and so that the proximal extremity 48 terminates in a region immediately prior to the portion 22b of the flexible elongate member 22 as shown in FIG. 2.

The port 32 which has been formed in the distal extremity of the flexible elongate member 22 as shown in FIG. 2, also extends through the tip valve 41 and the distal extremity 47 of the balloon 46 so that it is open to ambient.

A fitting assembly 51 is provided on the proximal extremity 23 of the flexible elongate member 22 and consists of first and second female and male Luer-type fittings 52 and 53 respectively mounted upon extension tube assemblies 54 and 56. The tubular assemblies 54 and 56 are comprised of an inner tube 57 and an outer reinforcing shrink tube 58. The extension assemblies 54 and 56 are inserted into the lumens 27 and 26 in the proximal extremity 23 of the flexible elongate member 22 and are secured therein by suitable means such as an adhesive or potting compound 61 as shown particularly in FIG. 4. Alternatively, the extension assemblies can be secured by insert molding using heat fusion.

Operation and use of the double lumen retroperfusion catheter 21 may now be briefly described as follows. The catheter is introduced into a venous vessel of a patient in a manner conventionally used in retroperfusion procedures. During the procedure, blood will flow through and into the male Luer-type fitting 53 and into the large lumen 26 and through the holes 31 to automatically inflate the balloon 46 to its maximum diameter. Blood at the same time will flow through the tip valve 41 and into the vessel of the patient. Pressure monitoring can occur by measuring the pressure of the blood appearing in the port 32 and extending through the lumen 27 to the female Luer-type fitting 52 which can be connected to a suitable pressure gauge.

From the foregoing description it can be seen that a large lumen 26 is used for retroperfusion and that the balloon 46 is automatically inflated during blood flow. The secondary lumen 27 terminates in the side port 32 which is used for pressure monitoring. The positioning of the side port prevents a pressure wave from the forward flow of retroperfusion blood from interfering with the pressure measurement. With the side port 32 arranged in a side position, the forward flow of blood through the tip valve 41 has very little, if any, effect upon the pressure measurement to make it possible to obtain relatively clean pressure signals.

The tip valve 41 of the present invention has construction features which are particularly advantageous. The four leaflets which are provided have a relatively low preload to maintain and yieldably urge the leaflets into a closed position. There is therefore very little pressure drop in a fluid such as blood passing through the tip valve to thereby provide the minimum of forward flow resistance. Upon reverse flow, the leaflets will readily move to a closed position to stop reverse flow. In addition, the soft walls of the tip valve will collapse and form a liquid-tight seal to further ensure that there is no reverse flow. This facilitates the rapid and complete deflation of the balloon 46. It also inhibits mixing of venous blood with arterial blood and to prevent venous blood from flowing into and through the catheter. The tip valve helps to prevent the auto-inflatable balloon from being accidentally inflated by hemostatic pressures which may occur in the blood vessel.

In addition, the construction of the tip valve is advantageous in that it permits the use of a guidewire to aid in the positioning of the retroperfusion catheter during its insertion into the venous vessel of the patient. The leaflets permit the guidewire to be advanced and retracted therethrough without damaging the valve.

The tip valve 41 has a rounded distal extremity which is quite soft so that there is reduced danger of penetrating a vessel wall as the retroperfusion catheter is being advanced into the vessel of the patient. The softness of the tip valve permits the tip valve to act as a shock absorber or bumper as the catheter is being advanced and thus provides a flexible tip for the catheter.

Another embodiment of the retroperfusion catheter of the present invention is a triple lumen retroperfusion catheter 71 shown in FIGS. 11 through 15. The catheter 71 is of the type which utilizes a non-auto-inflatable balloon in which the inflation of the balloon is controlled completely independently of the retroperfusion flow. The retroperfusion catheter 71 consists of a flexible elongate tubular member or element 72 which is extruded from a suitable material such as PeBax to provide a large lumen 73 and two small lumens 74 and 76 as shown in FIGS. 13 and 14. As shown in FIG. 13, the lumen 73 is substantially circular in cross section at the proximal end 77 of the tubular element 72 and is substantially D-shaped cross-section near the distal extremity 78 of the tubular element 72.

Extension tube assemblies 81, 82 and 83 are provided which are mounted in the lumens 73, 74 and 76 respectively in a suitable manner such as by use of a potting compound 84 or by heat fusion as hereinbefore described in connection with the previous embodiment. The flexible elongate member 72 is provided with an enlarged portion 72a in much the same manner as the flexible elongate element 22 was provided with an enlarged portion 22a in the previous embodiment so as to accommodate the extension tube assemblies 81, 82 and 83. Each of the extension tube assemblies 81, 82 and 83 is provided with a suitable fitting, as for example, a female or male Luer-type fitting 85 or 86. Thus a male fitting 85 is provided which is in communication with the lumen 73.

A balloon 87 formed of the same polyethylene material as hereinbefore described is provided which has proximal and distal extremities 88 and 89. The balloon 87 can be secured to the distal extremity of the tubular member 72 by suitable means such as by threads, a silicone adhesive, and in addition, or alternatively, by utilizing a heat shrinkable material with or without cyanoacrylate adhesive, it can be shrunk onto the tubular member 72 to provide a fluid-tight seal between the balloon 87 and the tubular member 72. An elongate slot 91 of a suitable length as, for example, 0.150 inches and a suitable width of 0.020 inches is provided in the tubular member 72 and opens into the balloon lumen 74 and into the interior of the balloon 87. Another slot 92 is provided in the tubular member 72 near the distal extremity 89 of the balloon and has a suitable width as, for example, 0.020 inches and a length of approximately 0.075 inches and opens into the pressure lumen 76.

A relatively soft tip or bumper 96 has been provided and is mounted on the distal extremity of the tubular member 72. It can be mounted in a manner very similar to the manner in which the tip valve 41 has been mounted. It also can be formed of a similar material. However, the leaflet portions 41a, 41b, 41c and 42d are not provided so that there is formed a large open passage 97 which is in communication with the large lumen 73 used for retroperfusion blood flow.

Operation and use of a triple lumen retroperfusion catheter 71 may now be briefly described as follows. The catheter 71 can be introduced into the venous vessel with or without the use of a guidewire. As can be appreciated, the guidewire can extend through the large lumen 73 provided for retroperfusion blood flow. The balloon 87 can be inflated through the slot 91 with a suitable gas such as carbon dioxide or helium through the balloon inflation and deflation lumen 74 to provide the desired amount of inflation. Retroperfusion blood can flow through the lumen 73 from a pump cassette which is provided for the retroperfusion blood flow. Pressure measurements can be readily made by attaching a suitable pressure gauge to the appropriate extension tube assembly and monitored through the port 92.

The construction of the retroperfusion catheter 71 with its very soft bumper or tip 96 makes it possible to position the catheter 71 with reduced danger of damaging or penetrating the side wall of the vessel into which the catheter 71 is being introduced. The very flexible tip also aids in steering the catheter as it is introduced into the vessel.

It is apparent from the foregoing that there has been provided a retroperfusion catheter which has distinct advantages over retroperfusion catheters heretofore provided. The tip construction which has been utilized is provided with a triple redundancy to ensure that the tip will not become separated from the distal extremity of the catheter. In addition, the tip construction is is very soft and pliable so that it will not cause damage to the venous vessel or penetrate the vessel as the catheter is being introduced. In one embodiment, the tip is constructed in such a manner so as to provide leaflets and flexible collapsible walls which readily prevent reverse flow but which provide very little resistance to forward flow of blood through the leaflets. The leaflets also permit the use of a guidewire for introducing the catheter when desired by permitting easy insertion and removal of the guide wire through the tip valve.

Although the catheter of the present invention has been described for use with retroperfusion, it should be appreciated that the catheter and tip construction can also be used for retroinfusion for the administration of pharmacological agents.

What is claimed is:

1. In a retroperfusion catheter, a flexible elongate element formed of plastic having proximal and distal extremities and having at least first and second lumens extending therethrough, a flexible tip formed of a material which is substantially softer than that of the flexible elongate element secured to the distal extremity of the flexible elongate element, a balloon having proximal and distal portions carried by the distal extremity of the flexible elongate element, the distal portion of the balloon overlying a portion of the flexible tip and securing the flexible tip to the distal extremity of the flexible elongate member to ensure that the flexible tip will not become separated from the distal extremity of the flexible elongate element.

2. A catheter as in claim 1 together with an adhesive disposed between said portion of said flexible tip and the distal position of the balloon.

3. A catheter as in claim 2 wherein the distal extremity of the flexible elongate element is provided with screw-like threads and wherein said portion of the flexible tip is provided with threads which interfit with the threads on the distal extremity of the catheter to provide additional redundancy to ensure that the flexible tip will not become separated from the catheter.

4. A catheter as in claim 1 wherein said tip is provided with a flow passage in communication with the first lumen in the flexible elongate element.

5. A catheter as in claim 4 wherein said flexible tip is provided with yieldable and flexible leaflets normally closing said flow passage in said flexible tip.

6. A catheter as in claim 5 wherein said leaflets in a closed position in combination have a hemispherical configuration.

7. A catheter as in claim 5 wherein the flexible tip is provided with at least two flexible leaflets.

8. A catheter as in claim 1 together with a flow passage in the flexible elongate element and establishing communication between the first lumen and the interior of the balloon so that the balloon can become automatically inflated upon the flow of retroperfusion blood through the first lumen.

9. A catheter as in claim 8 wherein the distal extremity of the catheter is provided with a side opening port spaced proximally from the tip and in communication with the second lumen in the flexible elongate element.

10. A catheter as in claim 1 wherein the catheter is provided with a third lumen and wherein retroperfusion blood flows through the first lumen, wherein the flexible elongate element is provided with at least one hole establishing communication between the second lumen and the interior of the balloon and at least one hole proximal of the flexible tip and in communication with the third lumen.

11. A catheter as in claim 10 together with a fitting assembly secured to the proximal extremity of the flexible elongate element and having a fitting in communication with each of the lumens.

12. A catheter as in claim 1 wherein a single lumen is provided for retroperfusion blood flow and balloon auto inflation.

* * * * *